(12) United States Patent
Chong (10) Patent No.: US 11,759,621 B2
(45) Date of Patent: Sep. 19, 2023

(54) CARDIAC PUMP

(71) Applicant: Triphasic Cardiac Pump Pty Ltd., Kallaroo (AU)

(72) Inventor: Albert Yoonsong Chong, Kallaroo (AU)

(73) Assignee: Triphasic Cardiac Pump Pty Ltd., Kallaroo (AU)

( * ) Notice: Subject to any disclaimer, the term of this patent is extended or adjusted under 35 U.S.C. 154(b) by 737 days.

(21) Appl. No.: 16/961,710

(22) PCT Filed: Jan. 10, 2019

(86) PCT No.: PCT/AU2019/050010
§ 371 (c)(1),
(2) Date: Jul. 13, 2020

(87) PCT Pub. No.: WO2019/136520
PCT Pub. Date: Jul. 18, 2019

(65) Prior Publication Data
US 2021/0361928 A1 Nov. 25, 2021

(30) Foreign Application Priority Data

Jan. 11, 2018 (AU) ................................ 2018900086
Apr. 10, 2018 (AU) ................................ 2018901176

(51) Int. Cl.
*A61M 60/279* (2021.01)
*A61M 60/851* (2021.01)
(Continued)

(52) U.S. Cl.
CPC ........ *A61M 60/279* (2021.01); *A61M 60/113* (2021.01); *A61M 60/36* (2021.01);
(Continued)

(58) Field of Classification Search
CPC .. A61M 60/279; A61M 60/446; A61M 60/36; A61M 60/113; A61M 60/284; A61M 2205/106
See application file for complete search history.

(56) References Cited

U.S. PATENT DOCUMENTS 4,976,593 A  12/1990  Miyamoto
5,188,604 A  2/1993  Orth
(Continued)

FOREIGN PATENT DOCUMENTS

CN    104841029 A    3/2015
DE    19816120 C1    6/1999
(Continued)

OTHER PUBLICATIONS

International Search Report and Written Opinion Form PCT/ISA210 and PCT/ISA/237, International Application PCT/AU2019/050010, pp. 1-11 International Filing Date Jan. 10, 2019, dated Mar. 8, 2019.

*Primary Examiner* — Katherine H Schwiker
*Assistant Examiner* — Rachel T. Smith
(74) *Attorney, Agent, or Firm* — George McGuire (57) ABSTRACT

A cardiac pump is arranged to mimic triphasic operation. The pump uses a fluid line formed from flexible tubing, along with a reciprocating actuator arranged to move between a free orientation and an occluding orientation. This allows a portion of the fluid line to be selectively occluded during movement of the actuator, enabling blood or other fluids to be peristaltically forced fluid towards a fluid outlet. The direction of operation of the actuator, and the selection of appropriate occluding or free orientations, allows the pump to be operated in a triphasic manner.

18 Claims, 5 Drawing Sheets

(51) Int. Cl.
  *A61M 60/446* (2021.01)
  *A61M 60/38* (2021.01)
  *A61M 60/113* (2021.01)
  *A61M 60/36* (2021.01)

(52) U.S. Cl.
  CPC .......... *A61M 60/38* (2021.01); *A61M 60/446* (2021.01); *A61M 60/851* (2021.01)

(56) References Cited

U.S. PATENT DOCUMENTS

| | | |
|---|---|---|
| 5,215,450 A | 6/1993 | Tamari |
| 5,716,318 A | 2/1998 | Mannin |
| 2009/0016915 A1 | 1/2009 | Caramuta |
| 2014/0257019 A1 | 9/2014 | Cook et al. |

FOREIGN PATENT DOCUMENTS

| | | | | |
|---|---|---|---|---|
| DE | 102016005467 A1 | 11/2017 | | |
| GB | 2036371 B | 1/1983 | | |
| WO | 2000035513 A2 | 6/2000 | | |
| WO | WO-03072161 A2 * | 9/2003 | .......... | A61M 1/1053 |
| WO | WO-2011003595 A1 * | 1/2011 | .......... | A61M 1/1005 |
| WO | 2016180951 A1 | 11/2016 | | |

* cited by examiner

CARDIAC PUMP

CROSS-REFERENCE TO RELATED APPLICATION

The present application is the United Stated National Stage Application of PCT Application No. PCT/AU2019/050010 filed on Jan. 10, 2019, which claims priority to Australian patent application Nos. 2018900086 filed on Jan. 11, 2018 and 2018901176 filed on Apr. 10, 2018, the disclosure of each of which is incorporated herein by reference in their its entirety.

FIELD OF THE INVENTION

The present invention relates to a cardiac pump, primarily arranged for use as part of a cardiopulmonary bypass profusion system or an extracorporeal membrane oxygenation system.

BACKGROUND TO THE INVENTION

Cardiac pumps used in surgery traditionally fall into two types: peristaltic and centrifugal. Both types of pump can be arranged to provide a consistent flow of blood at an appropriate pressure, with the pumps being adjustable to compensate for changes in flow rate or pressure requirements.

Traditional peristaltic pumps provide a pulsatile flow of blood. Traditional centrifugal pumps provide a steady flow of blood. These has proved to be sufficient to maintain a patient through surgery.

It is notable, however, that the flow of blood provided by such cardiac pumps is notably different to the aortic flow provided by a beating heart. Natural aortic flow is triphasic in nature: through systolic, early diastolic and late diastolic phases. Traditional cardiac pumps do not replicate this flow.

The effects of pulsatile or steady pumping of blood rather than triphasic flow during open heart surgery are not well understood. It is at least possible that using a pump which more closely replicates patient physiology will lead to improved patient outcomes. It is also considered valuable to provide such a pump for use within a laboratory setting, to enable further testing to be done.

The present invention seeks to provide a cardiac pump which mimics a natural triphasic aortic flow.

A further disadvantage of cardiac pumps used in surgery is that pump heads are generally single-use items, as it is impractical to completely clean all blood residue from a pump. This represents a significant expense in cardiac surgery.

SUMMARY OF THE INVENTION

According to one aspect of the present invention there is provided a cardiac pump having a fluid line formed from flexible tubing, the fluid line having a first portion which acts as an inlet line, a second connecting portion, and a third portion which acts as a return line, the cardiac pump having a reciprocating actuator, the actuator having a first actuating member arranged to move between a free orientation and an occluding orientation such that the first actuating member at least partially occludes the fluid line when in its occluding orientation; the cardiac pump being operable such that when the actuator moves away from an inlet the first actuating member may be in its occluding orientation so as to peristaltically force fluid towards a fluid outlet.

According to a second aspect of the present invention there is provided a cardiac pump having a fluid line formed from flexible tubing, the fluid line having a first portion which acts as an inlet line, a second connecting portion, and a third portion which acts as a return line, the cardiac pump having a reciprocating actuator, the actuator having a first actuating member arranged to move between a free orientation and an occluding orientation such that the first actuating member at least partially occludes the first portion of the fluid line when in its occluding orientation; the actuator having a second actuating member arranged to move between a free orientation and an occluding orientation such that the second actuating member at least partially occludes the third portion of the fluid line when in its occluding orientation; the cardiac pump being operable such that when the actuator moves away from an inlet the first actuating member may be in its occluding orientation so as to peristaltically force fluid towards a fluid outlet, and when the actuator moves towards the inlet the second member may be in its occluding orientation so as to peristaltically force fluid towards the fluid outlet.

The first portion and the third portion may each be generally linear and parallel to each other, with the actuator being moveable in a linear manner.

Alternatively, the first portion and the third portion may be arcuate, with the actuator being movable in a rotational manner.

The actuator may be a single moving body on which both the first actuating member and the second actuating member are mounted. Alternatively, the actuator may have two independently moving bodies, with the first actuating member mounted on a first actuator body and the second actuating member mounted on a second actuator body.

It is preferred that the actuator is arranged to have a long stroke and at least one short stroke. In a preferred embodiment, the long stroke corresponds to close to the length of the first and third portions of the inlet line, and the short stroke represents about 5% to 25% of the length of the long stroke (adjustable based on patient physiology). The arrangement is such that the actuator moves in a forward direction through a long stroke; in a reverse direction through a first short stroke (typically about 20% of the length of the long stroke); in the forward direction through a second short stroke shorter than the first short stroke (typically about 5% of the length of the long stroke); in the reverse direction through a long stroke; in the forward direction through a first short stroke; and in the reverse direction through a second short stroke to return to the starting position. It will be appreciated that this 'long, short, shorter' pattern represents a triphasic operation.

In a preferred mode of operation the actuator has its first member in the occluding orientation and its second member in the free orientation during a long stroke away from the pump inlet and the immediately following two short strokes; and then has the orientations of the first and second members reversed for the long stroke towards the pump inlet and the immediately following two short strokes.

The cardiac pump may include a check valve associated with the pump inlet. The check valve may be moveable between a first orientation in which it acts as a one-way valve and a second orientation in which it acts as a two-way valve. The arrangement is such that the check valve is in its first orientation during a long stroke of the actuator and during a second short stoke of the actuator, and is in its second orientation during a first short stroke of the actuator. The cardiac pump may include a similar check valve associated with the pump outlet.

It is preferred that the actuator is mounted on a linear screw drive. Alternatively, a belt-driven linear drive or a rack-and-pinion linear slide can be used.

Each of the first and second members of the actuator may be rollers mounted on cams. In a preferred embodiment of the invention, each cam is controlled by a stepper motor.

BRIEF DESCRIPTION OF THE DRAWINGS

It will be convenient to further describe the invention with reference to preferred embodiments of the present invention. Other embodiments are possible, and consequently the particularity of the following discussion is not to be understood as superseding the generality of the preceding description of the invention. In the drawings.

DETAILED DESCRIPTION OF PREFERRED EMBODIMENTS

Figure 1:
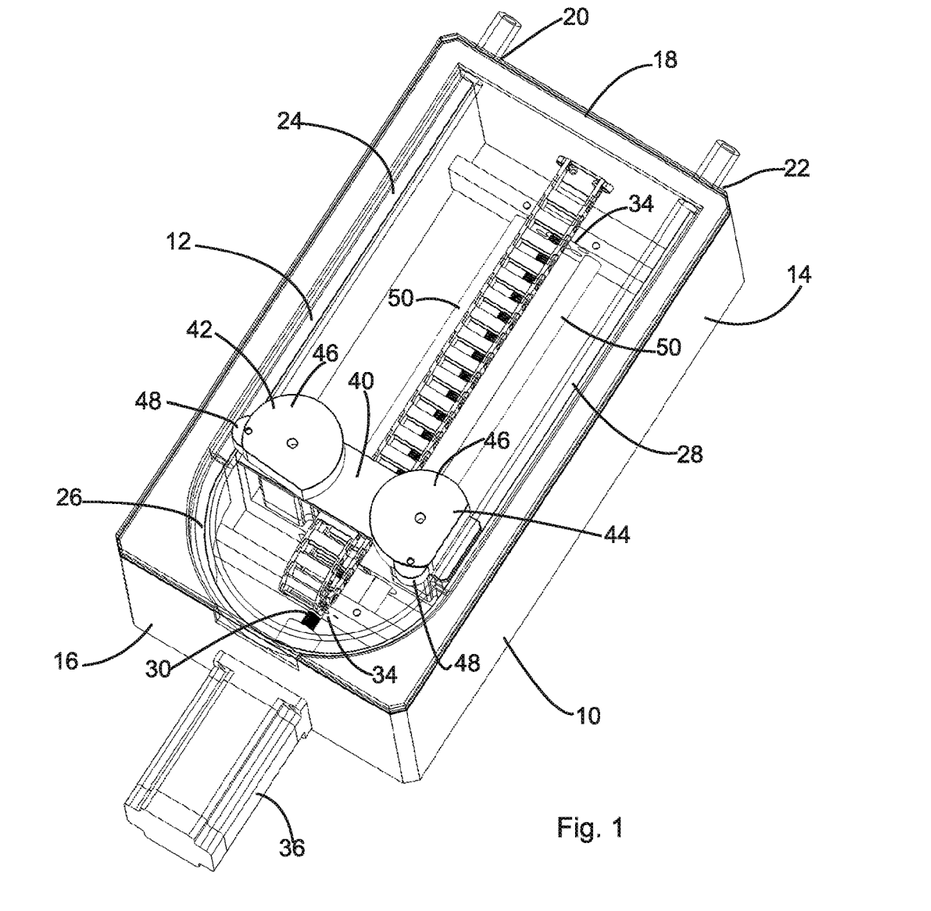
FIG. 1 is a perspective of a cardiac pump in accordance with the present invention.
Figure 2:
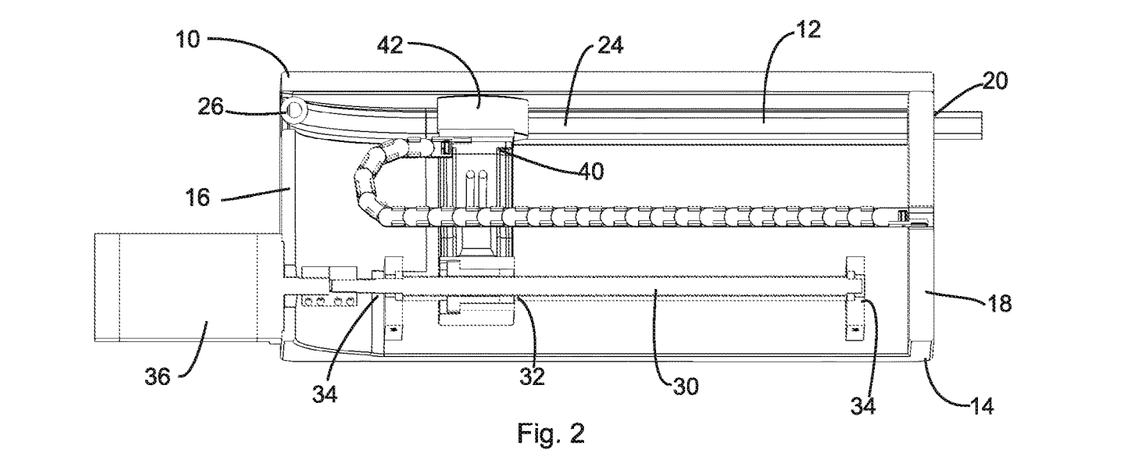
FIG. 2 is a cross-section through the cardiac pump of FIG. 1.

Referring to FIGS. 1 to 3, there is shown a pump 10. The pump 10 is arranged to force fluid (notionally blood) through a tube 12. In this embodiment the tube 12 is formed from platinum coated silicone tubing having an internal diameter of 19 mm. It is considered that bio-compatible tubing having an internal diameter between 6 mm and 25 mm may be suitable for this purpose.

The pump 10 has a generally rectangular outer housing 14, having a front wall 16 and a rear wall 18. The pump 10 has a fluid entry 20 and a fluid exit 22 both located near the top of the rear wall 18.

The tube 12 has a straight first tube portion 24 which extends from the fluid entry 20 along an internal side wall of the housing 14; a U-shaped second tube portion 26 which bends through 180° internally of the front wall 16; and a straight third tube portion 28 which extends along an internal side wall of the housing 14 to the fluid exit 22. The first tube portion 24 and the third tube portion 28 are parallel to each other, and are spaced across the housing 14.

A linear drive system is located along the base of the housing 14. The drive system is a ball screw drive system, including a driving screw 30 on which is located a ball nut 32. The driving screw 30 is parallel to the first and third tube portions 24, 28 of the tube 12, and is mounted in bearings 34 located respectively near the front wall 16 and the rear wall 18. The driving screw 30 is driven by a stepper motor 36 located outside the front wall 16. The arrangement is such that driving of the driving screw 30 by the motor 36 causes linear movement of the ball nut 32.

An actuator 40 is mounted atop the ball nut 32. The actuator 40 has a first actuating member 42 located towards the first tube portion 24 and a second actuating member 44 located towards the third tube portion 28.

The actuating members 42, 44 each include a roller 46 mounted on a cam member 48. The actuating members 42, 44 are controllable such that the cam members 48 can each be independently rotated between a free orientation in which the cam member 48 and roller 46 are clear of the respective tube portion 24, 28, and an occluding orientation in which the roller 46 impinges against the respective tube portion 24, 28. It is preferred that the roller 46 has a total travel distance of 19 mm and thus acts to fully occlude the tube 12. In FIG. 1, the first actuating member 42 is shown in its occluding orientation occluding the first tube portion 24 and the second actuating member 44 is shown in its free orientation clear of the third tube portion 28.

Two guide rods 50 are associated with the actuator 40 and are arranged to constrain movement of the actuator 40 in the linear direction.

Operation of the pump 10 will now be described with reference to FIGS. 3a to 3f.

The pump 10 generally operates to pump fluid such as blood in a peristaltic fashion from the fluid entry 20 to the fluid exit 22. It does this in one of two ways: by moving the actuator from near the rear wall 18 in the direction of the front wall 16 with the first actuating member 42 in its occluding orientation and the second actuating member 44 in its free orientation; and by moving the actuator from near the front wall 16 in the direction of the rear wall 18 with the first actuating member 42 in its free orientation and the second actuating member 44 in its occluding orientation.

It will be appreciated that the pump 10 can be continuously operated in such a fashion, providing a continuous (monophasic) pumping operation.

It is preferred that the pump 10 be operated in a triphasic manner, replicating the action of the human heart.

In such a mode the pump 10 operates in a six-step cycle, beginning in the position where the actuator 40 is close to the rear wall 18. In steps one to three (drawings 3a to 3c), the first actuating member 42 is in its occluding orientation and the second actuating member 44 is in its free orientation. In steps four to six (drawings 3d to 3f), the first actuating member 42 is in its free orientation and the second actuating member 44 is in its occluding orientation.

Figure 3A:
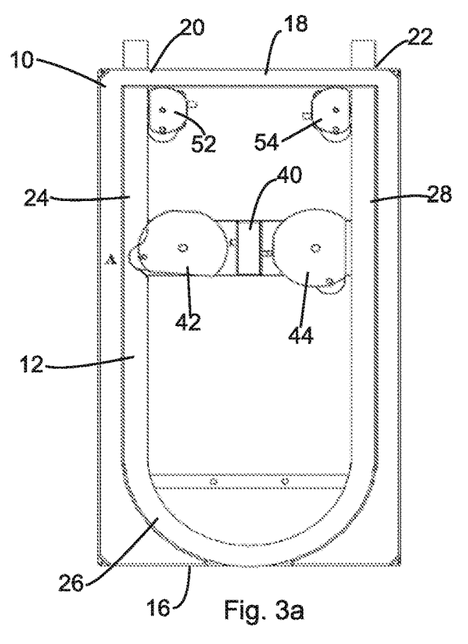
FIGS. 3a to 3f are a sequential series of plan views showing the operation of the cardiac pump of FIG. 1.

In step one as shown in FIG. 3a, the actuator 40 is driven in a long stroke the full length of travel towards the front wall 16. This mimics the systolic phase of normal cardiac function.

Figure 3B:
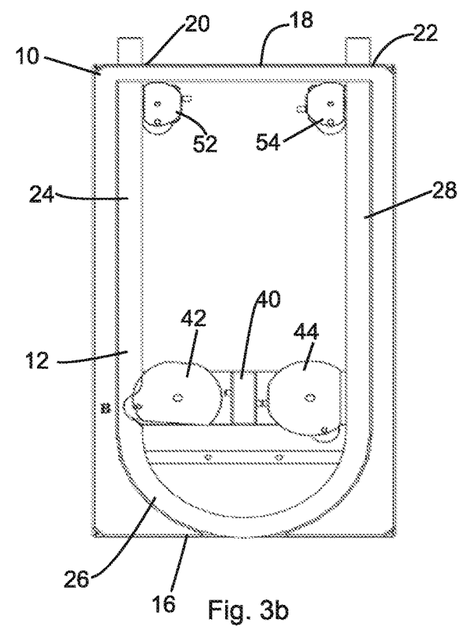

In step two, shown in FIG. 3b, the actuator 40 is driven in a short stroke (about 20% of the full length of travel) back towards the rear wall 18. This mimics the early diastolic phase of cardiac function. The actual length of this short stroke can be chosen to reflect an individual patient's physiology.

Figure 3C:
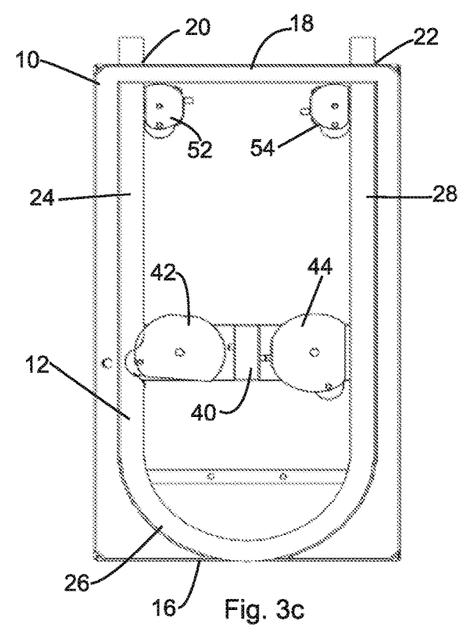

In step three, shown in FIG. 3c, the actuator 40 is driven in a still shorter stroke (about 5% of the full length of travel) back towards the front wall 16. This mimics the late diastolic phase of cardiac function, and is also adjustable for an individual patient.

Figure 3D:
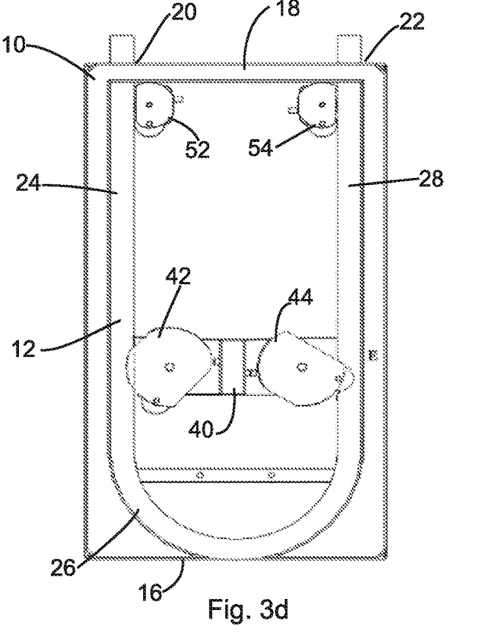

In step four, shown in FIG. 3d, the actuator 40 is driven in a long stroke the full length of travel towards the rear wall 18. This mimics the next systolic phase of normal cardiac function.

Figure 3E:
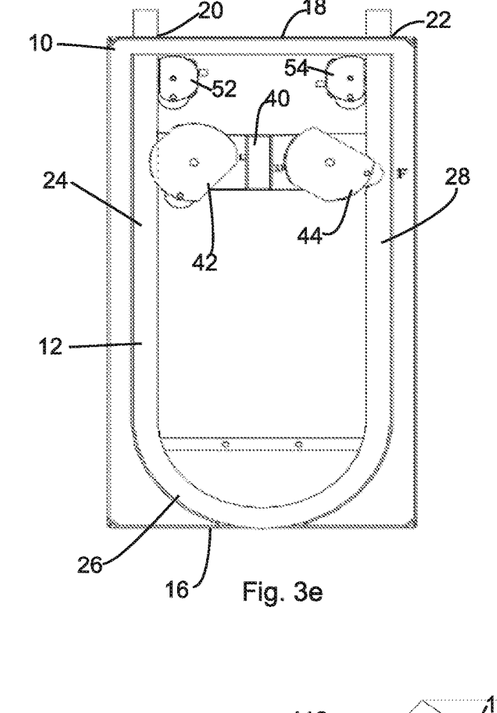

In step five, shown in FIG. 3e, the actuator 40 is driven in a short stroke (about 20% of the full length of travel) back towards the front wall 16. This mimics the early diastolic phase of cardiac function.

Figure 3F:
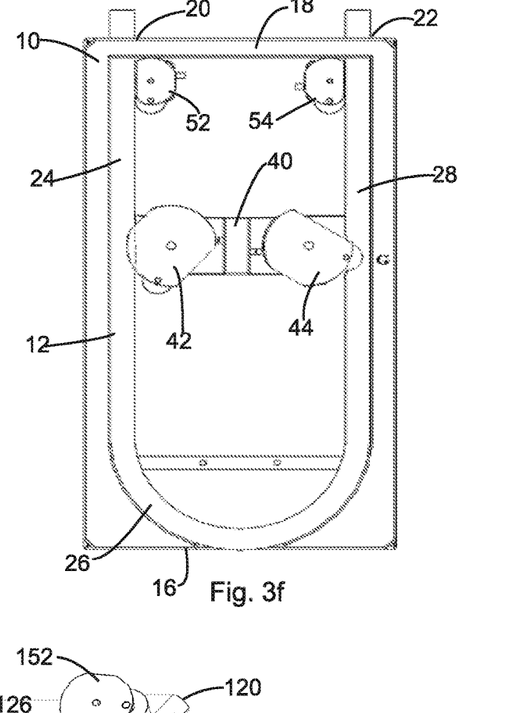

In step six, shown in FIG. 3f, the actuator 40 is driven in a shorter stroke back towards the rear wall 18. This mimics the late diastolic phase of cardiac function.

The cycle then repeats.

In order for correct flow rates and pressures to be maintained, a first valve 52 is associated with both the fluid entry 20 and a second valve 54 is associated with the fluid exit 22. The valves 52, 54 are structured so as to operate as one-way valves during the long strokes (i.e. the systolic phase) and the shortest strokes (i.e. the late diastolic phase), but to permit reverse flow (i.e. negative pressure) during the early diastolic phase.

It will be appreciated that actual reverse flow may not be useful in all settings. Although it may be valuable in a laboratory setting, reverse flow may not be prudent in a clinical environment. It is anticipated that the pump 10 may be operated in 'long stroke-rest-short stroke' mode to simulate triphasic flow without a negative pressure stage.

Figure 4:
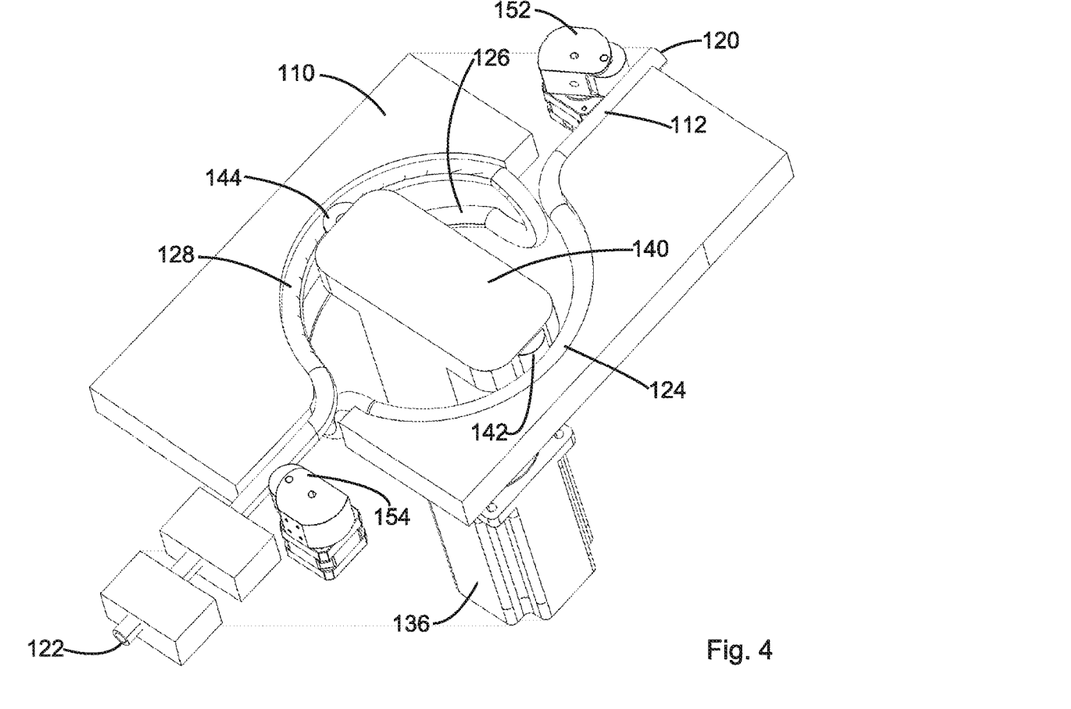
FIG. 4 is an indicative perspective of a second embodiment of a cardiac pump in accordance with the present invention.

FIG. 4 shows an alternative cardiac pump 110. The cardiac pump 110 operates in a similar fashion to the cardiac pump 10, however the first tube portion 124 and the third tube portion 128 are both circular, with the second tube portion 126 extending through a 180° arc to connect the first tube portion 124 and the third tube portion 128.

The actuator 140 is driven by a rotational motor 136. The first actuating member 142 and the second actuating member 144 work in similar fashion to the actuating members 42, 44 of the linear embodiment.

The operation of the pump 110 is broadly similar to that of the pump 10. Rather than each of the steps being measured as a linear stroke, the steps are measured as a rotation of the actuator 140. The first step is a clockwise rotation of about 100°; the second step a counter-clockwise rotation of about 20°; the third step a clockwise rotation of about 5°; fourth step a counter-clockwise rotation of about 100° (the drawing shows the position halfway through the fourth step); the fifth step a clockwise rotation of about 20°; and the sixth step a counter-clockwise rotation of about 5°. The first and second actuating members 142, 144 move between free and occluding orientations accordingly.

Figure 5:
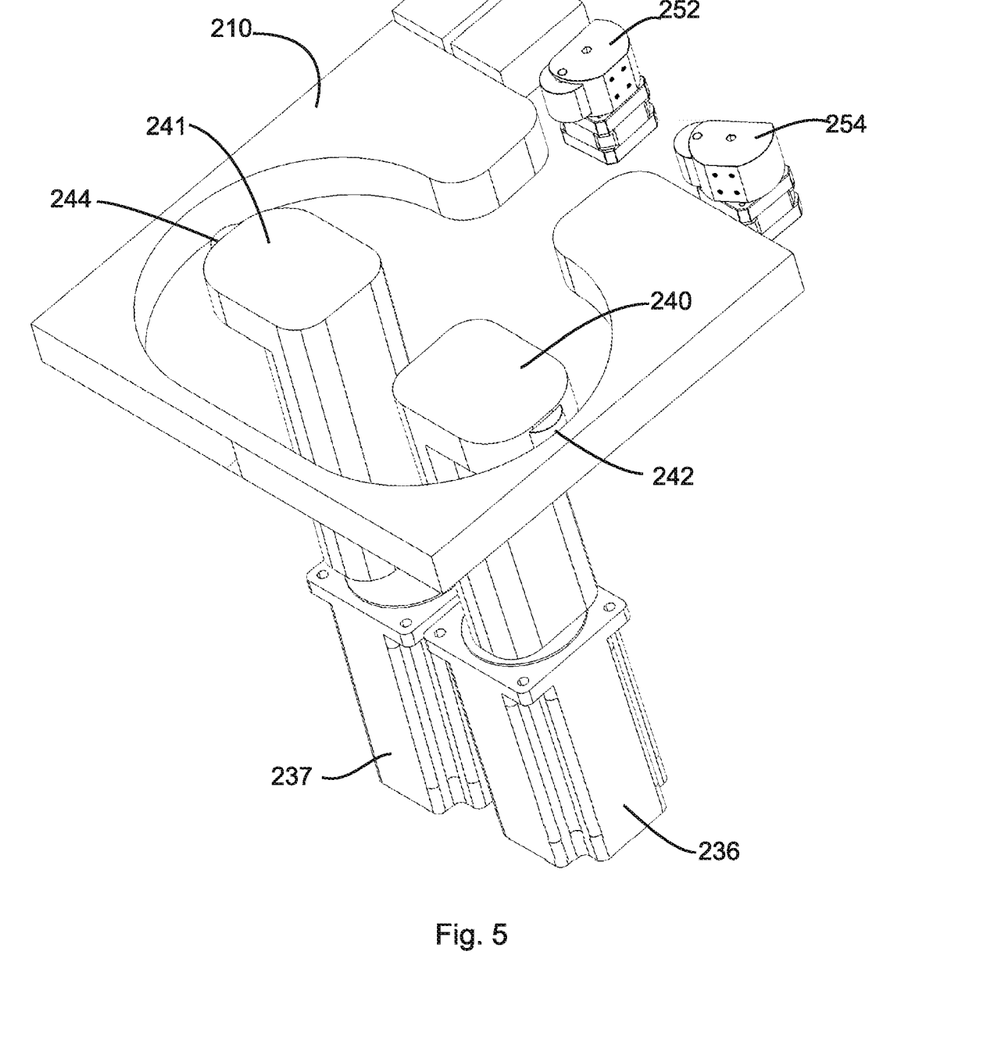
FIG. 5 is an indicative perspective of a third embodiment of a cardiac pump in accordance with the present invention.

FIG. 5 shows another alternative cardiac pump 210. This pump is similar to the pump 110, however the actuator 140 has been replaced with a first actuator body 240 powered by a first actuator motor 136 and a second actuator body 241 powered by a second actuator motor 137. This arrangement allows the first and second actuating members 242, 244 to be operated independently; that is, when the first actuating member 242 is in its occluding position (and working through steps 1-3 of the operation), the second actuating member 244 in its free position can be rotated into the correct 'start' position for step 4.

In this way the operation of the first and second actuating members 242, 244 can be in the same angular direction, simplifying the arrangement of the tubing (not shown).

Figure 6A:
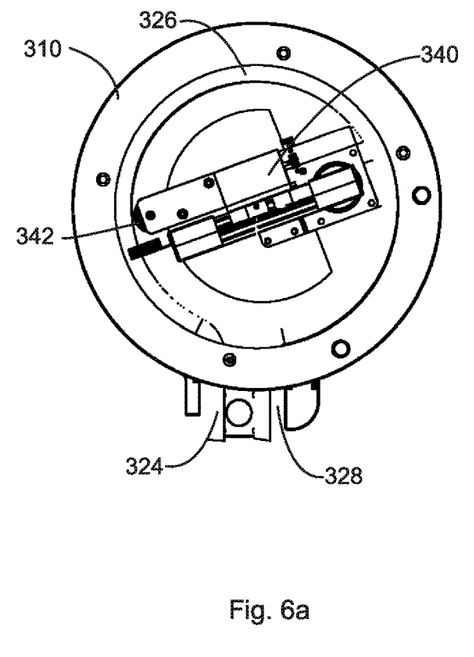
FIGS. 6a to 6d are a sequential series of plan views showing the operation of a cardiac pump in accordance with a further embodiment of the present invention.

FIG. 6a shows yet another alternative cardiac pump 310. This pump is similar to the pump 110, with an actuator 340 operating against second tube portion 326, the pump 310 having an inlet portion being a first tube portion 324 and an outlet being a third tube portion 328.

Figure 6B:
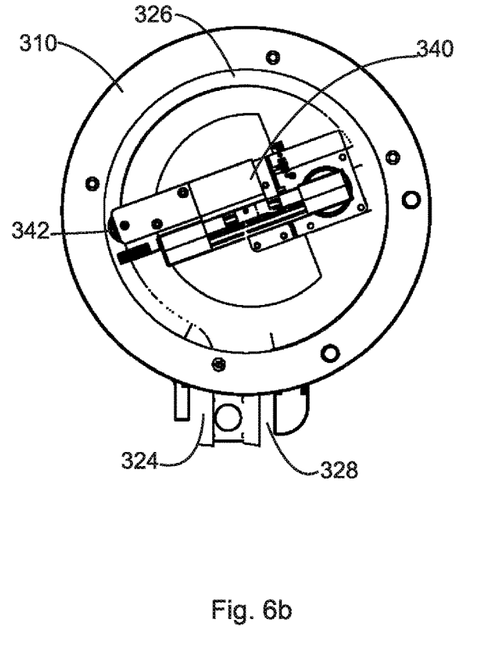
Figure 6C:
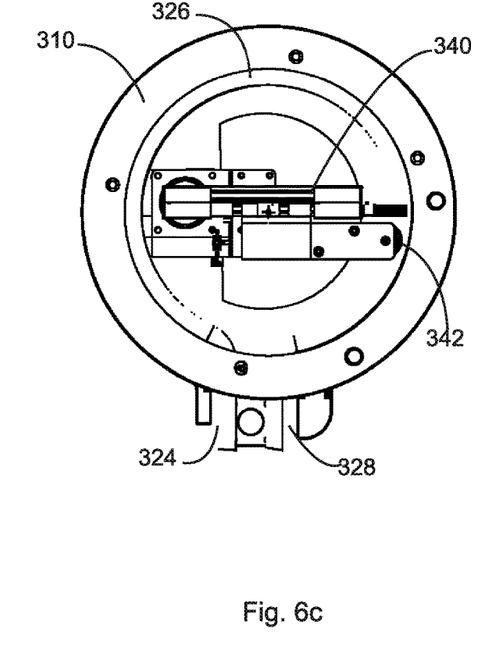
Figure 6D:
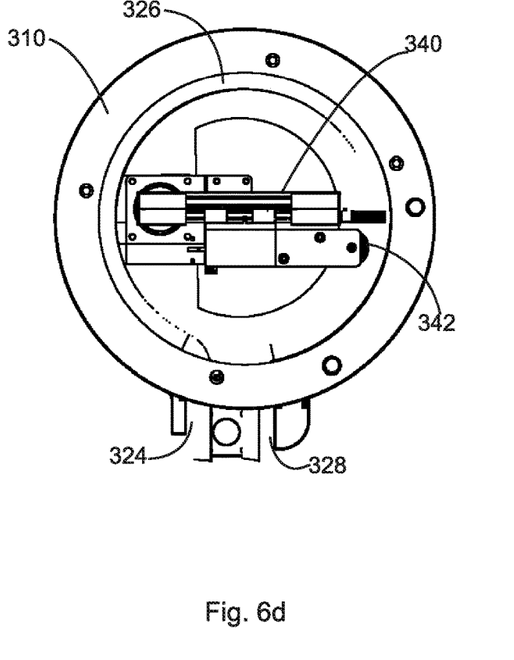

The actuator 340 has a single actuating member 342, moveable between a free orientation as shown in FIGS. 6a and 6d, and an occluding orientation as shown in FIGS. 6b and 6c. The arrangement is such that the actuator 340 moves through close to 180° with the actuating member 342 in its occluded orientation, and then is arranged to rapidly rotate through the remaining 180° (or slightly more) whilst the actuating member 342 is in its free orientation.

Modifications and variations as would be apparent to a skilled addressee are deemed to be within the scope of the present invention.

What is claimed is:

1. A cardiac pump having a fluid line formed from flexible tubing, the fluid line having a first portion which acts as an inlet line, a second connecting portion, and a third portion which acts as a return line, the cardiac pump having a reciprocating actuator, the actuator having a first actuating member arranged to move between a free orientation and an occluding orientation such that the first actuating member at least partially occludes the first portion of the fluid line when in the occluding orientation of the first actuating member; the actuator having a second actuating member arranged to move between a free orientation and an occluding orientation such that the second actuating member at least partially occludes the third portion of the fluid line when in the occluding orientation of the second actuating member; the cardiac pump being operable such that when the actuator moves away from an inlet the first actuating member may be in the occluding orientation of the first actuating member so as to peristaltically force fluid towards a fluid outlet, and when the actuator moves towards the inlet the second actuating member may be in the occluding orientation of the second actuating member so as to peristaltically force fluid towards the fluid outlet.

2. The cardiac pump as claimed in claim 1, wherein the first portion and the third portion are generally linear and parallel to each other, with the actuator being moveable in a linear manner.

3. The cardiac pump as claimed in claim 2, wherein the actuator is mounted on a linear screw drive.

4. The cardiac pump as claimed in claim 1, wherein the first portion and the third portion are arcuate, with the actuator being movable in a rotational manner.

5. The cardiac pump as claimed in claim 1, wherein the actuator is a single moving body on which both the first actuating member and the second actuating member are mounted.

6. A cardiac pump as claimed in claim 1, wherein the actuator has two independently moving bodies, with the first actuating member mounted on a first actuator body of the two independently moving bodies and the second actuating member mounted on a second actuator body of the two independently moving bodies actuator body.

7. The cardiac pump as claimed in claim 1, wherein the actuator is arranged to have a long stroke and at least one short stroke.

8. The cardiac pump as claimed in claim 7, wherein the long stroke corresponds to an entire length of the first and third portions of the fluid line, and the short stroke represents between 5% and 25% of the length of the long stroke.

9. The cardiac pump as claimed in claim 7, wherein the actuator is arranged to have a first short stroke and a second short stroke, the second short stoke being shorter than the first short stroke.

10. The cardiac pump as claimed in claim 9, wherein the actuator moves from a starting point in a forward direction through the long stroke; in a reverse direction through the first short stroke; in the forward direction through the second short stroke; in the reverse direction through the long stroke; in the forward direction through the first short stroke; and in the reverse direction through the second short stroke to return to the starting position.

11. A cardiac pump as claimed in claim 10, wherein the actuator has the first actuating member in the occluding orientation and the second actuating member in the free orientation during the long stroke wherein the actuator moves in the forward direction, and the immediately following first short stroke and second short stroke; and then has the first actuating member in the free orientation and the second actuating member in the occluding orientation during the long stroke wherein the actuator moves in the reverse direction, and the immediately following first short stroke and second short stroke.

12. The cardiac pump as claimed in claim 1, wherein the cardiac pump includes an inlet check valve associated with the inlet.

13. The cardiac pump as claimed in claim 12, wherein the inlet check valve is moveable between a first orientation in which the inlet check valve acts as a one-way valve and a second orientation in which the inlet check valve acts as a two-way valve.

14. The cardiac pump as claimed in claim 1, wherein the cardiac pump includes an outlet check valve associated with the fluid outlet.

15. The cardiac pump as claimed in claim 14, wherein the outlet check valve is moveable between a first orientation in which the outlet check valve acts as a one-way valve and a second orientation in which the outlet check valve acts as a two-way valve.

16. The cardiac pump as claimed in claim 1, wherein each of the first and second members of the actuator is a roller.

17. The cardiac pump as claimed in claim 16, wherein each roller is controlled by a cam.

18. A cardiac pump having a fluid line formed from flexible tubing, the fluid line having a first portion which acts as an inlet line, a second connecting portion, and a third portion which acts as a return line, the cardiac pump having a reciprocating actuator, the actuator having a first actuating member arranged to move between a free orientation and an occluding orientation such that the first actuating member at least partially occludes the fluid line when in the occluding orientation; the cardiac pump being operable such that when the actuator moves away from an inlet the first actuating member may be in the occluding orientation so as to peristaltically force fluid towards a fluid outlet.

* * * * *